(12) United States Patent
Lademann et al.

(10) Patent No.: US 11,510,857 B2
(45) Date of Patent: Nov. 29, 2022

(54) COSMETIC COMPOSITIONS HAVING ANTIOXIDANT PROPERTIES

(71) Applicant: SHANGHAI PECHOIN BIOTECH CO., LTD., Shanghai (CN)

(72) Inventors: Jürgen Lademann, Fürstenwalde (DE); Leonhard Zastrow, Monaco (MC); Martina Meinke, Berlin (DE); Stephanie Albrecht, Berlin (DE); Torsten Zuberbier, Kleinmachnow (DE); Alexandra Lan, Beijing (CN)

(73) Assignee: SHANGHAI PECHOIN BIOTECH CO., LTD, Shanghai (CN)

( * ) Notice: Subject to any disclaimer, the term of this patent is extended or adjusted under 35 U.S.C. 154(b) by 63 days.

(21) Appl. No.: 16/643,027

(22) PCT Filed: Aug. 30, 2018

(86) PCT No.: PCT/IB2018/000971
§ 371 (c)(1),
(2) Date: Feb. 28, 2020

(87) PCT Pub. No.: WO2019/043450
PCT Pub. Date: Mar. 7, 2019

(65) Prior Publication Data
US 2020/0188265 A1    Jun. 18, 2020

(30) Foreign Application Priority Data
Aug. 30, 2017 (DE) .......................... 102017119863.6

(51) Int. Cl.
| | | |
|---|---|---|
| *A61K 8/49* | (2006.01) |
| *A61K 8/9794* | (2017.01) |
| *A61K 8/9778* | (2017.01) |
| *A61K 8/9789* | (2017.01) |
| *A61K 8/25* | (2006.01) |
| *A61K 8/26* | (2006.01) |
| *A61K 8/27* | (2006.01) |
| *A61K 8/28* | (2006.01) |
| *A61K 8/29* | (2006.01) |
| *A61K 8/37* | (2006.01) |
| *A61K 8/41* | (2006.01) |
| *A61K 8/42* | (2006.01) |
| *A61K 8/44* | (2006.01) |
| *A61K 8/46* | (2006.01) |
| *A61K 8/58* | (2006.01) |
| *A61K 8/67* | (2006.01) |
| *A61Q 17/04* | (2006.01) |
| *A61Q 19/08* | (2006.01) |

(52) U.S. Cl.
CPC .............. *A61K 8/4966* (2013.01); *A61K 8/25* (2013.01); *A61K 8/26* (2013.01); *A61K 8/27* (2013.01); *A61K 8/28* (2013.01); *A61K 8/29* (2013.01); *A61K 8/37* (2013.01); *A61K 8/415* (2013.01); *A61K 8/42* (2013.01); *A61K 8/44* (2013.01); *A61K 8/466* (2013.01); *A61K 8/496* (2013.01); *A61K 8/585* (2013.01); *A61K 8/671* (2013.01); *A61K 8/673* (2013.01); *A61K 8/676* (2013.01); *A61K 8/9778* (2017.08); *A61K 8/9789* (2017.08); *A61K 8/9794* (2017.08); *A61Q 17/04* (2013.01); *A61Q 19/08* (2013.01); *A61K 2800/41* (2013.01); *A61K 2800/43* (2013.01); *A61K 2800/59* (2013.01)

(58) Field of Classification Search
CPC ...................................................... A61Q 17/04
See application file for complete search history.

(56) References Cited

U.S. PATENT DOCUMENTS

| | | | | |
|---|---|---|---|---|
| 5,587,148 A | * | 12/1996 | Mitchell | .................. A61K 8/27 |
| | | | | 424/59 |
| 7,892,523 B2 | * | 2/2011 | Golz-Berner | ............ A61K 8/44 |
| | | | | 424/59 |
| 2001/0031247 A1 | | 10/2001 | Josso et al. | |
| 2003/0053966 A1 | | 3/2003 | Richard | |
| 2006/0155007 A1 | | 7/2006 | Huber | |
| 2014/0154191 A1 | * | 6/2014 | Doucet | ..................... A61K 8/19 |
| | | | | 424/59 |
| 2015/0202145 A1 | * | 7/2015 | Friedman | ............... A61K 8/894 |
| | | | | 424/59 |
| 2015/0313820 A1 | * | 11/2015 | Kulke | .................... A61Q 19/10 |
| | | | | 424/48 |
| 2018/0036213 A1 | * | 2/2018 | Li | ......................... A61Q 19/00 |

FOREIGN PATENT DOCUMENTS

| | | | | |
|---|---|---|---|---|
| CN | 102525852 | | 7/2012 | |
| CN | 107028832 | | 8/2017 | |
| DE | 602 12 514 | | 6/2007 | |
| DE | 10 2007010861 | | 9/2008 | |
| DE | 10 2008 044 701 | | 3/2010 | |
| EP | 2129357 | | 12/2009 | |
| EP | 2921157 A1 | * | 9/2015 | .......... A61K 9/5089 |
| WO | WO 2016/087948 | | 6/2016 | |

OTHER PUBLICATIONS

Opinion on Titanium dioxide, Scientific Committee on Consumer Safety, Oct. 2020. (Year: 2020).*
Warheit, D. et al., "What is the impact of surface modifications and particle size on commercial titanium dioxide particle samples? A review of in vivo pulmonary and oral toxicity studies" Toxicology Letters 302 (2019) 42-99. (Year: 2019).*
International Search Report, PCT/IB2018/000971, dated Mar. 20, 2019.
Written Opinion, PCT/IB2018/000971, dated Mar. 20, 2019.
Fitzpatrick. T.B., "The Validity and Practicality of Sun-Reactive Skin Type-I Through Type-Vi," Arch.Dermatol. 124(6), 869-871 (1988).
Friebel, M. et al., "Determination of optical properties of human blood in the spectral range 250 to 1100 nm using Monte Carlo simulations with hematocrit-dependent effective scattering phase functions," Journal of Biomedical Optics 11(3), (2006).

(Continued)

*Primary Examiner* — Gina C Justice
(74) *Attorney, Agent, or Firm* — Nixon & Vanderhye

(57) ABSTRACT

The present invention relates to cosmetic compositions having antioxidant properties and suitable for any type of skin.

13 Claims, 2 Drawing Sheets

(56) References Cited

OTHER PUBLICATIONS

Herrline, T. et al., "Classification of cosmetic products—The Radical Protection Factor (RPF)," SOFW—Journal 5(124), 282-284 (1998).
Meinke, M. et al., "Radical Protection by Sunscreens in the Infrared Spectral Range," Photochemistry and Photobiology, 2011, 87:452-456.
Schroeder, P. et al., "Photoprotection beyond Ultraviolet Radiation—Effective Sun Protection Has to Include Protection against Infrared A Radiation-Induced Skin Damage," Skin Pharmacol Physiol. 2010;23(1):15-7.
Souza, C. et al., "Radical-Scavenging Activity of a Sunscreen Enriched by Antioxidants Providing Protection in the Whole Solar Spectral Range," Skin Pharmacol Physiol 30(2), 81-89 (2017).

\* cited by examiner

COSMETIC COMPOSITIONS HAVING ANTIOXIDANT PROPERTIES

BACKGROUND OF THE INVENTION

Field of the Invention

The invention relates to a cosmetic light protection and sunscreen agent having specific effectiveness with regard to certain skin types.

More generally, the invention relates to cosmetic compositions having antioxidant properties and suitable for any type of skin.

Description of the Related Art

A large number of sunscreen agents are known already, which usually contain UV filters for the UVA and UVB ranges as well as other components beneficial to the skin. In these agents, particular protective or stabilising effects are intended to be achieved by, for example, modified methyl pyrrolidones or by acrylic polymers with dextrin fatty acid esters or by triazines. Other publications describe the addition of plant extracts, such as in U.S. Pat. No. 7,892,523 B2, or encapsulation into photosensitive capsules, such as in WO 2016/087948 A2.

It is further known that free radicals are formed in the skin also in the visible and infrared spectral ranges and that cells and cell components can be destroyed by these highly reactive molecules (Schröder et al., Skin Pharmacol Physiol. 2010; 23(1):15-7). To address this, EP 2129357 proposes to use a mixture of UVA and UVB filters and sea buckthorn oil, particular types of glass or minerals and a radical scavenger as a light protection agent.

Little work has been done by the scientific community on full-range light protection.

SUMMARY OF THE INVENTION

The object of the present invention is to provide a cosmetic light protection and sunscreen agent which offers a specific and effective protection for dark skin types from radiation in the full range spectrum of light, i.e. in the infrared, visible and UV spectral ranges.

Another object of the invention is to provide compositions protecting against infrared, visible and UV radiations.

Another object of the invention is to provide compositions having good antioxidant properties.

Another object of the invention is to provide compositions containing natural extracts having good antioxidant properties.

Another object of the invention is to provide a method of protection specially designed for dark-skinned people, but which is also efficient for all types of skin.

Another object of the invention is the use of a light protection and sunscreen agent for dark skin types and providing a method for protecting the skin of dark-skinned people from radiation from the UV, IR and visible ranges of radiation with a light protection and sun screen agent.

A first object of the invention is a composition having antioxidant and visible and near infra-red light protection properties comprising or consisting in a mixture of the following substances, the respective percentages by weight being in relation to the total weight of the composition
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
c) one or more cooling agents at a percentage by weight from 0.1 to 20%,
d) one or more radical scavengers, selected from the group consisting of plants, plant extracts, vitamins, amino acids, flavonoids, carotinoids, α-hydroxy acids and mixtures thereof, at a percentage by weight from 0.1 to 48%, and
e) a residual percentage up to 100 wt % of cosmetic carriers, excipients, active substances and mixtures thereof.

The Inventors have unexpectedly found that dark-skinned people, and especially of phototypes IV-V, are more sensitive to visible and NIR (Near Infra-Red) radiations and consequently produce more ROS (Reactive Oxygen Species) than people with other phototypes, when exposed to said radiations.

In a particular embodiment, the composition of the invention comprises or consists in a mixture of the following substances, the respective percentages by weight being in relation to the total weight of the composition
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
c) one or more cooling agents at a percentage by weight from 0.1 to 20%,
d) one or more radical scavengers, selected from the group consisting of plants, plant extracts, vitamins, amino acids, flavonoids, carotinoids, α-hydroxy acids and mixtures thereof, at a percentage by weight from 0.1 to 5%, and
e) a residual percentage up to 100 wt % of cosmetic carriers, excipients, active substances and mixtures thereof.

In a particular embodiment, the composition of the invention comprises or consists in a mixture of the following substances, the respective percentages by weight being in relation to the total weight of the composition
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 3 to 6.5%,
c) one or more cooling agents at a percentage by weight from 0.5 to 4.5%,
d) one or more radical scavengers, selected from the group consisting of plants, plant extracts, vitamins, amino acids, flavonoids, carotinoids, α-hydroxy acids and mixtures thereof, at a percentage by weight from 2 to 48%, and
e) a residual percentage up to 100 wt % of cosmetic carriers, excipients, active substances and mixtures thereof.

In a particular embodiment, the composition of the invention is a cosmetic light protection and sunscreen composition.

In a particular embodiment, the composition of the invention is an anti-aging composition.

In a particular embodiment, the composition of the invention is an anti-dark spot composition.

In a particular embodiment, the composition of the invention is a composition wherein the UVA and UVB have a percentage by weight in relation to the total weight of the composition from 5 to 24%, in particular from 5 to 7%, from 7 to 10%, or from 7 to 15%, from 10 to 15%, from 15 to 20%, from 20 to 24%.

In a particular embodiment, the composition of the invention is a composition wherein the pigments have a percentage by weight in relation to the total weight of the composition from 2 to 30%, in particular from 2 to 3%, from 3 to 6.5%, from 6.5 to 7%, from 7 to 10%, from 10 to 15%, from 15 to 20%, from 20 to 25%, from 25 to 30%.

In a particular embodiment, the composition of the invention is a composition wherein the cooling agents have a percentage by weight in relation to the total weight of the composition from 0.1 to 20%, in particular from 0.1 to 0.5%, from 0.5 to 4.5%, from 4.5 to 7%, from 7 to 10%, from 10 to 13%, from 13 to 16%, from 16 to 20%.

In a particular embodiment, the composition of the invention is a composition wherein the radical scavengers have a percentage by weight in relation to the total weight of the composition from 0.05 to 48%, from 0.1 to 5%, in particular from 0.05 to 0.1%, from 0.1 to 0.5%, from 0.5 to 1%, from 1 to 2%, from 2 to 5%, from 5 to 10%, from 10 to 15%, from 15 to 20%, from 20 to 30%, from 30 to 40%, from 40 to 48%.

In a particular embodiment, the composition of the invention comprises or consists in a mixture of the following substances, the respective percentages by weight being in relation to the total weight of the composition
a) one or more UVA and UVB filters at a percentage by weight of 14.5%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
c) one or more cooling agents at a percentage by weight from 0.1 to 20%,
d) one or more radical scavengers, selected from the group consisting of plants, plant extracts, vitamins, amino acids, flavonoids, carotinoids, α-hydroxy acids and mixtures thereof, at a percentage by weight from 0.1 to 5%, and
e) a residual percentage up to 100 wt % of cosmetic carriers, excipients, active substances and mixtures thereof.

In a particular embodiment, the composition of the invention comprises or consists in a mixture of the following substances, the respective percentages by weight being in relation to the total weight of the composition
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight of 10.5%,
c) one or more cooling agents at a percentage by weight from 0.1 to 20%,
d) one or more radical scavengers, selected from the group consisting of plants, plant extracts, vitamins, amino acids, flavonoids, carotinoids, α-hydroxy acids and mixtures thereof, at a percentage by weight from 0.1 to 5%, and
e) a residual percentage up to 100 wt % of cosmetic carriers, excipients, active substances and mixtures thereof.

In a particular embodiment, the composition of the invention comprises or consists in a mixture of the following substances, the respective percentages by weight being in relation to the total weight of the composition
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
c) one or more cooling agents at a percentage by weight of 16%,
d) one or more radical scavengers, selected from the group consisting of plants, plant extracts, vitamins, amino acids, flavonoids, carotinoids, α-hydroxy acids and mixtures thereof, at a percentage by weight from 0.1 to 5%, and
e) a residual percentage up to 100 wt % of cosmetic carriers, excipients, active substances and mixtures thereof.

In a particular embodiment, the composition of the invention comprises or consists in a mixture of the following substances, the respective percentages by weight being in relation to the total weight of the composition
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
c) one or more cooling agents at a percentage by weight from 0.1 to 20%,
d) one or more radical scavengers, selected from the group consisting of plants, plant extracts, vitamins, amino acids, flavonoids, carotinoids, α-hydroxy acids and mixtures thereof, at a percentage by weight of 0.18%, and
e) a residual percentage up to 100 wt % of cosmetic carriers, excipients, active substances and mixtures thereof.

In a particular embodiment, the composition of the invention can be used in association with another anti-aging agent.

In a particular embodiment, the composition of the invention can be used in association with a whitening agent.

In a particular embodiment, the composition of the invention can be used in association with another anti-aging agent and a whitening agent.

In a particular embodiment, the composition of the invention is a composition wherein the UV filters are Bis-Ethylhexyloxyphenol Methoxyphenyl Triazine, Drometrizole Trisiloxane, Terephthalylidene Dicamphor Sulfonic Acid, Ethylhexyl Triazone, Butyl Methoxydibenzoylmethane, Diethylamino Hydroxybenzoyl Hexyl Benzoate, Diethylhexyl Butamido Triazone, Phenylbenzimidazole Sulfonic Acid, Ethylhexyl Methoxycinnamate, Ethylhexyl Salicylate, Methylene Bis-Benzotriazolyl Tetramethylbutylphenol, Octocrylene, Phenylbenzimidazole Sulfonic Acid, or mixtures thereof.

In a particular embodiment, the composition of the invention is a composition wherein the pigment is a mixture of $TiO_2$ and ZnO, each with small and larger particle sizes, wherein in weight 2 to 5 parts of $TiO_2$ and 1 to 2 parts of ZnO are present, each with particle sizes from 100 to 500 µm, and 12 to 24 parts of $TiO_2$ and 8 to 10 parts of ZnO are present, each with particle sizes from 10 to 600 nm.

In a particular embodiment, the composition of the invention is a composition wherein the pigment is a mixture of nanometer-size particles and micrometer-size particles in a weight ratio of the nanoparticles to the microparticles from 5:1 to 8:1.

In a particular embodiment, the composition of the invention is a composition wherein the smaller particle size is within the range from 10 to 300 nm and the larger particle size within the range from 100 to 250 µm.

In a particular embodiment, the composition of the invention is a composition wherein the pigment is TiO$_2$ with a particle size in the range from 10 to 600 nm.

In a particular embodiment, the composition of the invention is a composition wherein the pigment is a mixture of TiO$_2$ with 10 to 600 nm and TiO$_2$ with 100 to 500 µm and wherein the weight ratio of the nanoparticles to the microparticles is from 5:1 to 10:1.

In a particular embodiment, the composition of the invention is a composition wherein the pigment is a mixture containing at least nanoparticles.

In a particular embodiment, the composition of the invention is a composition wherein the pigment is a mixture of only nanoparticles.

In a particular embodiment, the composition of the invention comprises or consists in a mixture of the following substances, the respective percentages by weight being in relation to the total weight of the composition
a) one or more UVA and UVB filters at a percentage by weight of 12.5%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight of 7.5%,
c) one or more cooling agents at a percentage by weight of 15.1%,
d) one or more radical scavengers, selected from the group consisting of plants, plant extracts, vitamins, amino acids, flavonoids, carotinoids, α-hydroxy acids and mixtures thereof, at a percentage by weight of 0.12%, and
e) a residual percentage up to 100 wt % of cosmetic carriers, excipients, active substances and mixtures thereof.

In a particular embodiment, the composition of the invention comprises or consists in a mixture of the following substances, the respective percentages by weight being in relation to the total weight of the composition
a) one or more UVA and UVB filters at a percentage by weight of 14.5%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight of 10.5%,
c) one or more cooling agents at a percentage by weight of 16%,
d) one or more radical scavengers, selected from the group consisting of plants, plant extracts, vitamins, amino acids, flavonoids, carotinoids, α-hydroxy acids and mixtures thereof, at a percentage by weight of 0.18%, and
e) a residual percentage up to 100 wt % of cosmetic carriers, excipients, active substances and mixtures thereof.

In a particular embodiment, the composition of the invention is a composition wherein the cooling agent is selected from the group consisting of L-Menthone Glycerol Ketal, DL-Menthone Glycerol Ketal, mixtures of the two, N-Ethyl-p-Menthane-3-Carboxamide, Menthol, Isopulegol, Monomenthyl Glutarate, 3-L-Menthoxypropane-1,2-Diol, Ethoxycarbonylmethyl-3-p-Menthane Carboxamide, essential oils of camphor, mint, lavender and mixtures thereof.

In a particular embodiment, the composition of the invention is a composition wherein the radical scavenger, either on its own or in a mixture of scavengers, has a radical protection factor of 40 to 100,000.

In a particular embodiment, the composition of the invention is a composition wherein the radical scavenger, either on its own or in a mixture of scavengers, has a radical protection factor of 40 to 40,000.

In a particular embodiment, the composition of the invention is a composition wherein the radical scavenger, either on its own or in a mixture of scavengers, has a radical protection factor of 500 to 100,000.

In a particular embodiment, the composition of the invention has a radical protection factor of 20 to 4,000, preferably of 900 to 3600, in particular of 1100 to 3000.

In a particular embodiment, the composition of the invention has a sun protection factor higher than 40, in particular of 40 to 50+.

In a particular embodiment, the composition of the invention is a composition wherein the radical scavenger is an hydrophilic compound.

In a particular embodiment, the composition of the invention is a composition wherein the radical scavenger is selected from the group consisting of roseroot (*Rhodiola sacra* Root Extract or *Rhodiola Rosea* extract), Job's tear (*Coix Lacryma-Jobi* Seed Extract), orchid (*Dendrobium nobile* Lindl Flower Extract), Saussurea (*Saussurea involucrata* Extract), common marigold (*Calendula officinalis* Flower Extract), peony (*Paeonia lactiflora* Root Extract), Scutellaria (*Scutellaria lateriflora* Root Extract or *Scutellaria baicalensis* Extract), Salvia (*Salvia miltiorrhiza* Root Extract), orchid (*Bletilla striata* Root Extract), green tea (*Camellia sinensis* Leaf Extract), leucojum (*Leucojum aestivum* bulb extract), astragalus (*Astragalus membranaceus* root extract), saposhnikovia (*Saposhnikovia divaricata* root extract), albizia (*Albizia julibrissin* flower extract), gastrodia (*Gastrodia elata* root extract), *Magnolia seiboldii* extract, tocopheryl acetate and mixtures thereof.

In a particular embodiment, the composition of the invention is a composition wherein the radical scavenger is a mixture of roseroot (*Rhodiola* Sacra Root Extract), Job's tear (*Coix Lacryma-Jobi* Seed Extract), orchid (*Dendrobium nobile* Lindl Flower Extract) and green tea (*Camellia sinensis* Leaf Extract).

In a particular embodiment, the composition of the invention is a composition wherein the radical scavenger is a mixture of *Saussurea* (*Saussurea involucrata* Extract), common marigold (*Calendula officinalis* Flower Extract), peony (*Paeonia lactiflora* Root Extract) and green tea (*Camellia sinensis* Leaf Extract).

In a particular embodiment, the composition of the invention is a composition wherein the radical scavenger is a mixture of *Scutellaria* (*Scutellaria lateriflora* Root Extract), *Salvia* (*Salvia miltiorrhiza* Root Extract), orchid (*Bletilla striata* Root Extract) and green tea (*Camellia sinensis* Leaf Extract).

In a particular embodiment, the composition of the invention is a composition wherein the UV filters are a mixture of Ethylhexyl Methoxycinnamate, Diethylamino Hydroxybenzoyl Hexyl Benzoate, Bis-Ethylhexyloxyphenol Methoxyphenyl Triazine, Octocrylene and Phenylbenzimidazole Sulfonic Acid.

In a particular embodiment, the composition of the invention is a composition wherein the pigments are a mixture of titanium dioxide and zinc oxide.

In a particular embodiment, the composition of the invention is a composition wherein the cooling agent is menthol.

In a particular embodiment, the composition of the invention is a composition wherein the radical scavengers are a mixture of green tea extract, *Scutellaria baicalensis* extract, *Saussurea involucrata* extract, *Leucojum aestivum* bulb extract, *Astragalus membranaceus* root extract, *Saposhnik-*

*ovia divaricata* root, extract, *Calendula officinalis* flower extract, *Albizia julibrissin* flower extract and *Gastrodia elata* root extract.

In a particular embodiment, the composition of the invention is a composition wherein the UV filters are a mixture of Ethylhexyl Methoxycinnamate, Diethylamino Hydroxybenzoyl Hexyl Benzoate, Bis-Ethylhexyloxyphenol Methoxyphenyl Triazine, Octocrylene and Phenylbenzimidazole Sulfonic Acid, the pigments are titanium dioxide and zinc oxide, the cooling agent is menthol, the radical scavengers are a mixture of green tea extract, *Scutellaria baicalensis* extract, *Saussurea involucrata* extract, *Leucojum aestivum* bulb extract, *Astragalus membranaceus* root extract, *Saposhnikovia divaricata* root, extract, *Calendula officinalis* flower extract, *Albizia julibrissin* flower extract and *gastrodia elata* root extract.

In a particular embodiment, the composition of the invention is in a form of milk, gel, lotion, stick, water in oil emulsion, oil in water emulsion, or fluid emulsion.

For the preparation of the different forms previously listed, the following list of gelling agents can be used: carbomer, xanthan gum, carrageenan, guar gum and derivatives, cellulose derivatives, polyvinyl pyrrolidone, polyvinyl alcohol polyacrylates.

The compositions of the invention are stable at least for 6 months, notably 6 months, at room temperature.

In the sense of the invention, the term "room temperature" refers to a temperature of about 20° C. to about 25° C.

Emulsifiers that can be used for the above-mentioned cosmetic forms are for example: addition products of ethylene oxide with linear $C_8$-$C_{22}$ fatty alcohols, with $C_{12}$-$C_{22}$ fatty acids and with $C_8$-$C_{15}$ alkylphenols; $C_{12}$-$C_{22}$ fatty acid mono- and diesters of addition products of ethylene oxide with glycerol.

Other emulsifiers that can be used for the above-mentioned cosmetic forms are for example: addition products of ethylene oxide with castor oil; esters of $C_{12}$-$C_{22}$ fatty acids and glycerol, polyglycerol, pentaerythritol, sugar alcohols (for example sorbitol), polyglucosides (for example cellulose); polyalkylene glycols; wool wax alcohols; copolymers of polysiloxane-polyalkyl polyethers.

A second object of the invention is the use as a light protection and sunscreen composition of a mixture of the following substances, the respective percentages by weight being in relation to the total weight of the composition
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
c) one or more cooling agents at a percentage by weight from 0.1 to 20%,
d) one or more radical scavengers, selected from the group consisting of plants, plant extracts, vitamins, amino acids, flavonoids, carotinoids, α-hydroxy acids and mixtures thereof, at a percentage by weight from 0.05 to 48%, and
e) a residual percentage up to 100 wt % of cosmetic carriers, excipients, active substances and mixtures thereof for protecting the skin of people of skin types IV and V.

In a particular embodiment, in the use as a light protection and sunscreen composition of a mixture of the following substances, the respective percentages by weight being in relation to the total weight of the composition are:
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
c) one or more cooling agents at a percentage by weight from 0.1 to 20%,
d) one or more radical scavengers, selected from the group consisting of plants, plant extracts, vitamins, amino acids, flavonoids, carotinoids, α-hydroxy acids and mixtures thereof, at a percentage by weight from 0.1 to 5%, and
e) a residual percentage up to 100 wt % of cosmetic carriers, excipients, active substances and mixtures thereof.

In a particular embodiment, in the use as a light protection and sunscreen composition of a mixture of the following substances, the respective percentages by weight being in relation to the total weight of the composition are:
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 3 to 6.5%,
c) one or more cooling agents at a percentage by weight from 0.5 to 4.5%,
d) one or more radical scavengers, selected from the group consisting of plants, plant extracts, vitamins, amino acids, flavonoids, carotinoids, α-hydroxy acids and mixtures thereof, at a percentage by weight from 2 to 48%, and
e) a residual percentage up to 100 wt % of cosmetic carriers, excipients, active substances and mixtures thereof.

A third object of the invention is the use as an anti-aging composition of a mixture of the following substances, the respective percentages by weight being in relation to the total weight of the composition
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
c) one or more cooling agents at a percentage by weight from 0.1 to 20%,
d) one or more radical scavengers, selected from the group consisting of plants, plant extracts, vitamins, amino acids, flavonoids, carotinoids, α-hydroxy acids and mixtures thereof, at a percentage by weight from 0.05 to 48%, and
e) a residual percentage up to 100 wt % of cosmetic carriers, excipients, active substances and mixtures thereof for protecting the skin of people of skin types IV and V.

In a particular embodiment, in the use as an anti-aging composition of a mixture of the following substances, the respective percentages by weight being in relation to the total weight of the composition are:
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
c) one or more cooling agents at a percentage by weight from 0.1 to 20%,
d) one or more radical scavengers, selected from the group consisting of plants, plant extracts, vitamins, amino acids, flavonoids, carotinoids, α-hydroxy acids and mixtures thereof, at a percentage by weight from 0.1 to 5%, and e) a residual percentage up to 100 wt % of cosmetic carriers, excipients, active substances and mixtures thereof.

In a particular embodiment, in the use as an anti-aging composition of a mixture of the following substances, the respective percentages by weight being in relation to the total weight of the composition are:

a) one or more UVA and UVB filters at a percentage by weight from 5 to 24% b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 3 to 6.5%, c) one or more cooling agents at a percentage by weight from 0.5 to 4.5%, d) one or more radical scavengers, selected from the group consisting of plants, plant extracts, vitamins, amino acids, flavonoids, carotinoids, α-hydroxy acids and mixtures thereof, at a percentage by weight from 2 to 48%, and e) a residual percentage up to 100 wt % of cosmetic carriers, excipients, active substances and mixtures thereof.

Another object of the invention is the use of an anti-dark spot composition of a mixture of the following substances, the respective percentages by weight being in relation to the total weight of the composition a) one or more UVA and UVB filters at a percentage by weight from 5 to 24% b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%, c) one or more cooling agents at a percentage by weight from 0.1 to 20%, d) one or more radical scavengers, selected from the group consisting of plants, plant extracts, vitamins, amino acids, flavonoids, carotinoids, α-hydroxy acids and mixtures thereof, at a percentage by weight from 0.05 to 48%, and e) a residual percentage up to 100 wt % of cosmetic carriers, excipients, active substances and mixtures thereof for protecting the skin of people of skin types IV and V.

In a particular embodiment, in the use as an anti-dark spot composition of a mixture of the following substances, the respective percentages by weight being in relation to the total weight of the composition are:

a) one or more UVA and UVB filters at a percentage by weight from 5 to 24% b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%, c) one or more cooling agents at a percentage by weight from 0.1 to 20%, d) one or more radical scavengers, selected from the group consisting of plants, plant extracts, vitamins, amino acids, flavonoids, carotinoids, α-hydroxy acids and mixtures thereof, at a percentage by weight from 0.1 to 5%, and e) a residual percentage up to 100 wt % of cosmetic carriers, excipients, active substances and mixtures thereof.

In a particular embodiment, in the use as an anti-dark spot composition of a mixture of the following substances, the respective percentages by weight being in relation to the total weight of the composition are:

a) one or more UVA and UVB filters at a percentage by weight from 5 to 24% b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 3 to 6.5%, c) one or more cooling agents at a percentage by weight from 0.5 to 4.5%, d) one or more radical scavengers, selected from the group consisting of plants, plant extracts, vitamins, amino acids, flavonoids, carotinoids, α-hydroxy acids and mixtures thereof, at a percentage by weight from 2 to 48%, and e) a residual percentage up to 100 wt % of cosmetic carriers, excipients, active substances and mixtures thereof.

In a particular embodiment, the uses of the compositions of the invention can be done in association with another anti-aging agent.

In a particular embodiment, the uses of the compositions of the invention can be done in association with a whitening agent.

In a particular embodiment, the uses of the compositions of the invention can be done in association with another anti-aging agent and a whitening agent.

In a particular embodiment, in the uses of the invention, the pigment is a mixture of $TiO_2$ and ZnO with small and larger particle sizes, wherein in weight 2 to 5 parts of $TiO_2$ and 1 to 2 parts of ZnO are present, each with particle sizes from 100 to 500 μm, and 12 to 24 parts of $TiO_2$ and 8 to 10 parts of ZnO are present, each with particle sizes from 10 to 600 nm.

In a particular embodiment, in the uses of the invention, the radical scavenger is selected from the group consisting of roseroot (*Rhodiola sacra* Root Extract), Job's tear (*Coix Lacryma-Jobi* Seed Extract), orchid (*Dendrobium nobile* Lindl Flower Extract), *Saussurea* (*Saussurea involucrata* Extract), common marigold (*Calendula officinalis* Flower Extract), peony (*Paeonia lactiflora* Root Extract), *Scutellaria* (*Scutellaria lateriflora* Root Extract), *Salvia* (*Salvia miltiorrhiza* Root Extract), orchid (*Bletilla striata* Root Extract), green tea (*Camellia sinensis* Leaf Extract) and mixtures thereof.

In a particular embodiment, in the uses of the invention, the UV filters are a mixture of Ethylhexyl Methoxycinnamate, Diethylamino Hydroxybenzoyl Hexyl Benzoate, Bis-Ethylhexyloxyphenol Methoxyphenyl Triazine, Octocrylene and Phenylbenzimidazole Sulfonic Acid.

In a particular embodiment, in the uses of the invention, the pigments are a mixture of titanium dioxide and zinc oxide.

In a particular embodiment, in the uses of the invention, the cooling agent is menthol.

In a particular embodiment, in the uses of the invention, the radical scavengers are a mixture of green tea extract, *Scutellaria baicalensis* extract, *Saussurea involucrata* extract, *leucojum aestivum* bulb extract, *Astragalus membranaceus* root extract, *Saposhnikovia divaricata* root, extract, *Calendula officinalis* flower extract, *Albizia julibrissin* flower extract and *Gastrodia elata* root extract.

In a particular embodiment, in the uses of the invention, the UV filters are a mixture of Ethylhexyl Methoxycinnamate, Diethylamino Hydroxybenzoyl Hexyl Benzoate, Bis-Ethylhexyloxyphenol Methoxyphenyl Triazine, Octocrylene and Phenylbenzimidazole Sulfonic Acid, the pigments are titanium dioxide and zinc oxide, the cooling agent is menthol, the radical scavengers are a mixture of green tea extract, *Scutellaria baicalensis* extract, *Saussurea involu-* crata extract, *Leucojum aestivum* bulb extract, *Astragalus membranaceus* root extract, *Saposhnikovia divaricata* root, extract, *Calendula officinalis* flower extract, *Albizia julibrissin* flower extract and *Gastrodia elata* root extract.

Another object of the invention is the composition according to the invention for its use in the prevention of damages caused by free radicals on people, in particular dark-skinned people, more particularly of skin types IV and V.

Another object of the invention is a method for protecting the skin of people, in particular dark-skinned people, from radiation from the UV, IR and visible ranges of radiation with a light protection and sun screen composition comprising a mixture of the following substances, with percentages of weight in relation to the total weight of the composition
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
c) one or more cooling agents at a percentage by weight from 0.1 to 20%,
d) one or more radical scavengers, selected from the group consisting of plants, plant extracts, vitamins, amino acids, flavonoids, carotinoids, α-hydroxy acids and mixtures thereof, at a percentage by weight from 0.05 to 48%, and
e) a residual percentage up to 100 wt % of cosmetic carriers, excipients, active substances and mixtures thereof.

Another object of the invention is a method of cosmetic treatment consisting in applying on the skin of people, in particular dark-skinned people, more particularly of skin types IV and V, a composition according to the invention.

The cosmetic light protection and sunscreen agent according to the invention comprises a mixture of the following substances, the respective percentages by weight being in relation to the total weight of the agent
a) one or more UVA and UVB filters at a percentage by weight from 5 to 24%
b) one or more pigments, selected from the group consisting of rutile (titanium dioxide), zinc oxide, silicon dioxide, zirconium oxide, aluminium oxide and mixtures thereof with different particle sizes in the micro and nano ranges and at a percentage by weight from 2 to 7%,
c) one or more cooling agents at a percentage by weight from 0.5 to 4.5%,
d) one or more radical scavengers, selected from the group consisting of plants, plant extracts, vitamins, amino acids, flavonoids, carotinoids, α-hydroxy acids and mixtures thereof, at a percentage by weight from 2 to 48%, and
e) a residual percentage up to 100 wt % of cosmetic carriers, excipients, active substances and mixtures thereof.

It has been found that, as compared to light-skinned people, the formation of radicals in dark-skinned people is distinctly higher in the IR radiation range and a special sunscreen is required for this reason.

It has been further found that a mixture of UV filters, cooling agents, pigments and radical scavengers can achieve a distinctly improved protection in the overall range of UV and IR rays and in the range of visible light (UV+IR+Vis) for skin types IV and V as compared to a sunscreen agent of conventional composition. This is also true in comparison with such conventional agents which have very high sun protection factors of SPF 30 or 50. What matters here is not a larger number of filters and, thus, as it may seem, the sun protection factor SPF, but in fact the balance between UV filters, pigments, radical scavengers and a cooling agent.

The classification of skin types generally follows von Luschan's chromatic scale, derived with respect to the Fitzpatrick scale, which ranges from I to VI.
Skin type I=very light skin, freckles, light eyes, reddish blonde hair;
Skin type II: light skin, often freckles, light eyes, light hair;
Skin type III: medium-light skin, light or brown eyes, brown hair;
Skin type IV: brown skin, brown eyes, dark brown to black hair;
Skin type V: dark skin, brown eyes, dark brown to black hair;
Skin type VI: very dark skin, brown eyes, black hair.

See also I. Moll (Ed.) Dermatologie, Thieme Verlag 2005 p. 534 ff.

UVA, UVB and/or broadband filters can be used for the invention. These are, for example, Butyl Methoxy Dibenzoylmethane, 3-Benzylidene Camphor or sulphonic acid derivates thereof, Octyl Dimethyl PABA, Homosalate, Octisalate, Benzophenone-3, Benzophenone-4 and mixtures thereof.

UV filters with a low allergenic potential and without any hormonal side effects are particularly preferred, however. They are the following, which are used advantageously in a mixture of two or more: Bis-Ethylhexyloxyphenol Methoxyphenyl Triazine (Tinosorb S®), Drometrizole Trisiloxane (Mexoryl XL®), Terephthalylidene Dicamphor Sulfonic Acid (Mexoryl SX®), Ethylhexyl Triazone (Uvinul T 150®), Butyl Methoxydibenzoylmethane (Avobenzone®), Diethylamino Hydroxybenzoyl Hexyl Benzoate (Uvinul A Plus®), Diethylhexyl Butamido Triazone (Iscotrizinol®), Phenylbenzimidazole Sulfonic Acid (Enzulisol®).

Also preferred are mineral filters such as the oxides of Ti, Si, Zn, Fe(III), Zr, Al or Mn, which can also be used in a mixture with the chemical filters. Particle sizes are in the range of up to 500 μm, particularly preferably, however, in the range from 200 to 800 nm.

The mineral filters in this invention serve a double purpose, because they are used as pigments, in particular due to their reflective behaviour. In a particular embodiment of the invention, therefore, mixtures of the same or different pigments are used, with particle sizes in the range from 100 to 500 μm and particle sizes in the range from 400 to 800 nm in a ratio of 1:8 to 1:20 (large to small particle sizes).

It has been found that, due to the differences in particle sizes, a distinctly improved overall reflective behaviour of the pigments can be achieved, because the reflection in the UV and visible ranges decreases with increasing particle size, while the reflection in the infrared range increases. If, in addition, pigments are used which differ distinctly in their refractive indices, e.g. rutile n=2.80 and ZnO with n=2.10, the reflection will also increase.

A preferred pigment is therefore a mixture of $TiO_2$ and ZnO, each with small and larger particle sizes. Such a mixture is preferably a pigment mixture of $TiO_2$ and ZnO, wherein 2 to 5 parts of $TiO_2$ and 1 to 2 parts of ZnO are present, each with particle sizes from 200 to 500 μm, and 12 to 24 parts of $TiO_2$ and 8 to 10 parts of ZnO are present, each with particle sizes from 400 to 600 nm. In particular, this is, for example, a mixture of 2 parts of $TiO_2$ and 1 part of ZnO, each with particle sizes from 200 to 500 μm, and 12 parts of $TiO_2$ and 8 parts of ZnO, each with particle sizes from 400 to 600 nm. This already prevents, by reflection, a large part of the overall radiation from entering the skin and significantly improves the efficiency of the sunscreen preparation.

The pigments are preferably present in the range from 3 to 6.0 wt %, in particular 3.5 to 5.5 wt %.

A particularly preferred filter mixture consists of Butyl Methoxydibenzoylmethane and Bis-Ethylhexyloxyphenol Methoxyphenyl Triazine and $TiO_2/ZnO$ as the corresponding pigment, with weight ratios in the range from 1:2.2-2.8: 0.8-1.1 (filter to pigment ratio), wherein preferably the pigment is a mixture of $TiO_2$ and ZnO, each with small and larger particle sizes, wherein 2 to 5 parts of $TiO_2$ and 1 to 2 parts of ZnO are present, each with particle sizes from 200 to 500 m, and 12 to 24 parts of $TiO_2$ and 8 to 10 parts of ZnO are present, each with particle sizes from 400 to 600 nm.

In another embodiment of the invention the pigment is $TiO_2$ with a particle size in the range from 200 to 600 nm, in particular, however, a mixture of $TiO_2$ with 200 to 600 nm and $TiO_2$ with 100 to 500 μm, the nanoparticles and microparticles being present in a weight ratio of 5-10:1.

Preferred radical scavengers are plants and plant parts, in particular plant extracts. The preferred plant extracts include tannic acid, rosemary oil, rosemary extract, rosmarinic acid, green tea extract, grapefruit extract, curry extract, acerola extract, aronia skin extract, coffee bean extract, *angelica* root extract as well as extracts from the following plants: roseroot (*Rhodiola sacra* Root Extract), Job's tear (*Coix lacryma-Jobi* Seed Extract), orchid (*Dendrobium nobile* Lindl Flower Extract), *Saussurea* (*Saussurea involucrata* Extract), common marigold (*Calendula officinalis* Flower Extract), peony (*Paeonia lactiflora* Root Extract), *Scutellaria* (*Scutellaria* lateriflora Root Extract), *Salvia* (*Salvia miltiorrhiza* Root Extract), orchid (*Bletilla striata* Root Extract).

According to a preferred embodiment of the invention, the radical scavenger is a mixture of roseroot (*Rhodiola sacra* Root Extract), Job's tear (*Coix lacryma-Jobi* Seed Extract), orchid (*Dendrobium nobile* Lindl Flower Extract) and green tea (*Camellia sinensis* Leaf Extract).

According to another preferred embodiment of the invention, the radical scavenger is a mixture of *Saussurea* (*Saussurea involucrata* Extract), common marigold (*Calendula officinalis* Flower Extract), peony (*Paeonia lactiflora* Root Extract) and green tea (*Camellia sinensis* Leaf Extract).

According to a third preferred embodiment of the invention, the radical scavenger is a mixture of *Scutellaria* (*Scutellaria lateriflora* Root Extract), *Salvia* (*Salvia miltiorrhiza* Root Extract), orchid (*Bletilla striata* Root Extract) and green tea (*Camellia sinensis* Leaf Extract).

Regarding the radical scavengers of the three preferred embodiments, the distribution within the respective mixture is approximately equal, i.e. 1:1:1:1.

The radical scavengers of the preferred embodiments are present preferably at 2 to 12 wt %, relative to the weight of the light protection and sunscreen agent.

The plant extracts are prepared by extraction of the respective plant or the plant parts in fresh or dried form with water or water/glycerol at temperatures in the range from 15 to 35° C.

Other preferred radical scavengers are vitamins, such as vitamin C, vitamin A and B vitamins, and SOD (superoxide dismutase).

To become effective as envisaged by the invention, the radical scavengers, either on their own or as a mixture, have a radical protection factor of 500 to 100,000.

The radical protection factor (RPF) is a value which indicates the radical scavenging activity of a substance or a product containing antioxidants. It is measured, for example, using a MiniScope MS400 X-band EPR spectrometer produced by Magnettech, Berlin, Germany. The spin quantification of the reference sample DPPH (2,2-diphenyl-1-piperidylhydrazyl) (Sigma Aldrich, St. Louis, USA) is determined using a Bruker Elexsys E500 X-band EPR spectrometer produced by BioSpin GmbH, Karlsruhe, Germany, with a 1 mM DPPH solution in ethanol. The RPF measurement is performed at a constant temperature in the range from 25 to 50° C. against the reference sample of 1 mM DPPH, assisted by the software "MiniScopeControl 6.51.exe" with the following measurement parameters: BO-field: 3350.84 G; Sweep: 95.25 G; Sweep time: 20 s; Modulation: 2000 mG; MW atten: 15 dB; Gain: 1; E: 2; Smooth: 0.10 s; Steps: 4086.

The precise measurement method is described, for example, by Meineke et al. in Photochemistry and Photobiology, 2011, 87:452-456.

The number of reduced test radicals represents the radical scavenging activity, which is normalised to 1 mg of the measured product or the antioxidant. The RPF is calculated in accordance with the equation $$RPF = \frac{RC \times RF}{PI}$$

wherein RC is the concentration of the test radical [radicals per mg]; RF is the reduction factor determined by the difference between the intensity of the untreated test radical and the decreasing signal intensity after treatment with the antioxidant or the product, normalised to the signal of the untreated test radical; and PI is the product input represented by the amount of the measured product or the substance (antioxidant) [mg per ml].

By way of the positive number N, the RPF indicates the number of free radicals per mg, multiplied by 10 to the power of 14, i.e. RPF=N×[10 to the power of 14 radicals per mg]. In general, the value is often used in the literature without the 10 to the power of 14, as is also the case in the text of this specification.

The light protection and sunscreen agent according to the invention further contains a cooling component. Instead of actual cooling agents, humectants in the form of plant extracts are partly used as well. The cooling effect is improved, however, when using regular cooling agents selected from the group consisting of L-Menthone Glycerol Ketal (FEMA GRAS 3807), DL-Menthone Glycerol Ketal (FEMA GRAS 3808), mixtures of the two, N-Ethyl-3-p-Menthone Carboxamide (WS-5), Menthol, Isopulegol, monomenthyl glutarate, 3-L-Menthoxypropane-1,2-Diol (MPD), Ethoxycarbonylmethyl-3-p-Menthane Carboxamide (WS-5), essential oils of camphor, mint, lavender and mixtures thereof.

The cooling effect of water can also be used by adding cold creams with borax as an emulsifying aid.

The radical protection factor of a formulated light protection and sunscreen agent of the invention is within the range from 100 to 4000, preferably 900 to 3600, in particular 1100 to 3000.

The light protection and sunscreen preparation of the invention can be prepared as an O/W emulsion or as a W/O emulsion. For this purpose, known emulsifiers are used, for example C12-C22 fatty acid mono- and diesters of absorption products of 1 to 30 mol of ethylene oxide with glycerol for O/W emulsions or, for example, polyglycerol, pentaerythrite, polyethylene glycols or absorption products of 2 to 15 mol of ethylene oxide with castor oil for W/O emulsions.

The agent according to the invention further contains cosmetic excipients and carriers as are usually used in such preparations, e.g. water, preservatives, dyes, thickeners, plasticising substances, moisturising substances, fragrants, alcohols, polyols, electrolytes, polar and non-polar oils, polymers, copolymers, emulsifiers and/or stabilisers.

The oils used for the invention can be conventional cosmetic oils such as a mineral oil; hydrogenated polyisobutene (INCI name: Hydrogenated Polyisobutene); synthetic squalane or squalane prepared from natural products (INCI name: Squalane, e.g. Synthesqual®, Cosbiol®); cosmetic esters or ethers, which may be branched or unbranched, saturated or unsaturated; plant oils; or mixtures of two or more thereof.

Particularly suitable oils are, for example, Hydrogenated Polyisobutene, Polyisoprene, Squalane, Tridecyltrimellitate, Trimethylpropane-triisostearate, Isodecylcitrate, Neopentylglycol-diheptanoate, PPG-15-Stearylether, calendula oil, jojoba oil, avocado oil, macadamia nut oil or a mixture of several thereof. The cosmetic properties of the solid preparation, such as the degree of transparency, softness, hardness, spreading effect, are influenced depending on which oils are selected.

The cosmetic light protection and sunscreen agent of the invention can be used in the form of sun creams, sun gels, sun lotions, sun sprays or as sun milk. Such products are prepared in a way which is known to a person skilled in the art.

Object of the invention is also the use of a light protection and sunscreen agent of a mixture of the above described substances.

A further object of the invention is a method for protecting the skin of dark-skinned people from radiation from the UV, IR and visible ranges of radiation with an above described light protection and sun screen agent.

Radical production in subjects having different skin types was analysed in comparative analyses. In this study, subjects having a skin type of I to III were compared to subjects having a skin type of IV to V. The study showed that, within the ultraviolet spectral range, subjects having a light skin colour (skin types I to III) form significantly more radicals in their skin due to solar radiation. Subjects having a skin type of IV to V, on the other hand, show a distinctly lower formation of radicals. This is understandable, as the darker skin colour represents a protection system, similar to that which develops when subjects with light skin colour develop a tan.

While subjects with light and with dark skin colour hardly show any difference in the visible spectral range, the dark-skinned subjects, as compared to the light-skinned subjects, show a distinctly increased radical production in the infrared spectral range. It is twice as high as in light-skinned subjects.

Taking into account that more than 50% of the solar radiation reaches the skin in the infrared spectral range (thermal radiation), it becomes clear that effective protection also has to be provided for this range. The explanation for this effect is that dark-skinned subjects absorb much more infrared radiation, i.e. thermal radiation, and, due to this, the skin temperature of these subjects increases as compared to light-skinned subjects.

All figures given in percent or in parts in this specification are in relation to the weight.

The x-axis of the graph represents the wavelength in nanometers.

The y-axis of the graph represents the absorption or scattering coefficient in (1/mm).

Figure 2:
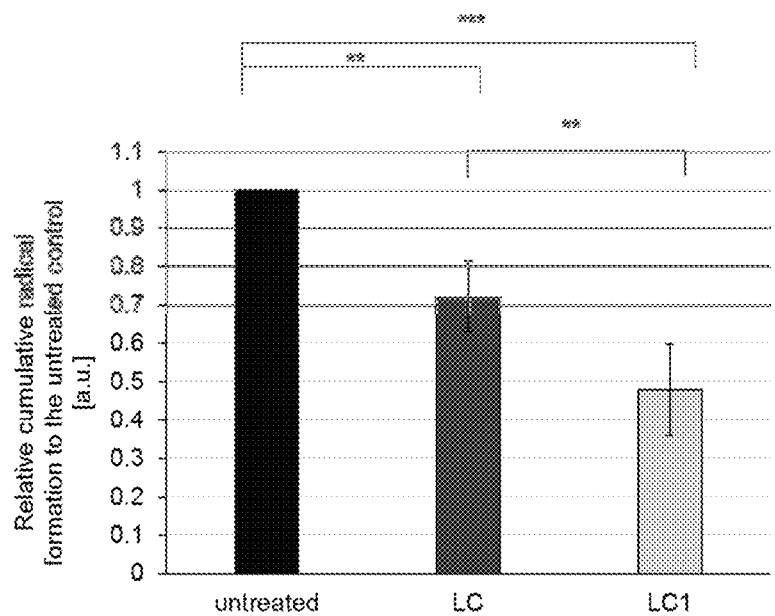

FIG. 2: Relative radical formation in the skin after irradiation with 42.6 J/cm$^2$ in the VIS/NIR spectral range. The data are calculated relative to the radical formation without any cream treatment, Mean±SEM,  $p \leq 0.01$, * $p \leq 0.001$.

The x-axis of the graph represents the 3 samples tested: the untreated control, LC and LC1.

The y-axis of the graph represents the relative cumulative radical formation to the untreated control in a.u.

Figure 3:
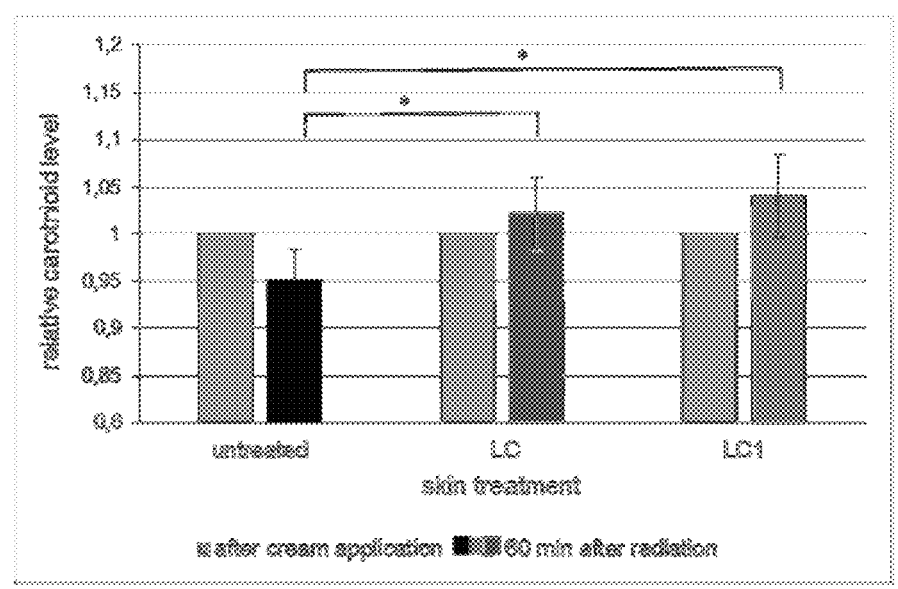

FIG. 3: Relative carotenoid concentration on the skin, before and after NIR irradiation (60 mW/cm$^2$) for untreated and sunscreen treated skin (LC1; LC, 2 mg/cm$^2$), * $p \leq 0.05$ (n=6).

The x-axis of the graph represents the 3 samples tested: the untreated control, LC and LC1.

The y-axis of the graph represents the relative carotenoid level.

The invention will now be explained in greater detail by way of examples.

DESCRIPTION OF THE PREFERRED EMBODIMENTS

Examples

Example 1

Light Protection and Sunscreen Formulation I

Three separately prepared phases, A, B and C, are formed. Phases A and B are stirred together at 75° C. and homogenised at this temperature for about 15 minutes at approximately 3000 rpm. After cooling down to 40° C., phase C is added while stirring, and stirring is continued for another few minutes. The phase composition, in wt %, is as follows.

Phase A: water up to 100%, Propylene Glycol 2.2, Acrylates Crosspolymer 0.5, Xanthan Gum 0.3.

Phase B: Ethylhexyl Methoxycinnamate 5.0, Tinosorb M® (Methylene Bis-Benzotriazolyl Tetramethylbutylphenol) 3.0, TiO$_2$ 4.0 (100 to 200 nm), TiO$_2$ 0.8 (200 to 300 m), ZnO 1.0 (100 to 200 nm), ZnO 0.2 (100 to 150 m), Ethylhexyl Salicylate 4.0, Butyl Methoxydibenzoylmethane 3.0, Dicaprylyl Carbonate 6.0.

Phase C: Colhibin® (Hydrolyzed Rice Protein) 0.5, mixture of antioxidant extracts 4.5 (rosewood (*Rhodiola sacra* Root Extract), Job's tear (*Coix lacryma-Jobi* Seed Extract), orchid (*Dendrobium nobile* Lindl Flower Extract) and green tea (*Camellia sinensis* Leaf Extract)), Isopulegol 2.0, Soy Protein 0.7, Preservative 0.8, Perfume 0.8.

Example 2

Light Protection and Sunscreen Formulation II

The preparation is similar to that of example 1. The phase composition, in wt %, is as follows.

Phase A: water up to 100%, Propylene Glycol 2.0, Acrylates Crosspolymer 0.6, Guar Gum 0.4.

Phase B: Mexoryl® XL (Drometrizole trisiloxane) 2.0, Mexoryl® SX (terephthalylidene dicamphor sulfonic acid) 1.0, Uvinul® T150 (Ethylhexyl Triazone) 2.0, Uvinul® A+(Diethylamino Hydroxybenzoyl Hexyl Benzoate) 2.80, TiO$_2$ 3.4 (100 to 200 nm), TiO$_2$ 0.4 (200 to 300 μnm), ZnO 0.4 (100 to 200 nm), ZnO 0.1 (100 to 150 m), Dicaprylyl Carbonate 5.5.

Phase C: Colhibin® (Hydrolyzed Rice Protein) 0.6, mixture of antioxidant extracts 4.5 (Saussurea (*Saussurea involucrata* Extract), common marigold (*Calendula officinalis* Flower Extract), peony (*Paeonia lactiflora* Root Extract) and green tea (*Camellia sinensis* Leaf Extract)), Glycerol 2.0, Menthol 1.0, Rice Protein 0.9, Preservative 0.8, Perfume 0.5.

Example 3

Light Protection and Sunscreen Formulation III

The preparation is similar to that of example 1. The phase composition, in wt %, is as follows.

Phase A: water up to 100%, Propylene glycol 2.1, Acrylates Crosspolymer 0.6, Guar Gum 0.4.

Phase B: Mexoryl® SX (terephthalylidene dicamphor sulfonic acid) 2.0, Uvinul® T150 (Ethylhexyl Triazone) 1.0, Avobenzone (Butyl Methoxydibenzoylmethane) 2.5, Enzulisol (Phenylbenzimidazole Sulfonic Acid) 1.6, $TiO_2$ 4.3 (100 to 300 nm), $TiO_2$ 0.6 (200 to 250 m), Dicaprilyl Carbonate 5.0.

Phase C: Colhibin® (Hydrolyzed Rice Protein) 0.5, mixture of antioxidant extracts 4.5 (*Scutellaria* (*Scutellaria lateriflora* Root Extract), *Salvia* (*Salvia miltiorrhiza* Root Extract), orchid (*Bletilla striata* Root Extract) and green tea (*Camellia sinensis* Leaf Extract)); N-Ethyl-3-p-Menthone Carboxamide 2.0, Urea 6.0; Soy Protein 0.9, Preservative 0.7, Perfume 0.9.

Example 4 Comparative Example

A sun protection cream I is applied to an area of skin of approximately 20 $cm^2$ in 10 dark-skinned subjects of skin type V, and a sun protection cream II to another area of similar size. The applied amount corresponds to the typical amount of 2 $mg/cm^2$. Both areas are exposed to IR radiation for a duration of 15 minutes and at an intensity of 70 $mW/cm^2$ using an LOT QuantumDesign solar simulator. After a break of another 5 minutes, the number of radicals formed is measured using the RPF method described above.

Sun protection cream I (commercial): UV filter Mexoryl® XL 2.0, Mexoryl® SX 1.0, Uvinul® T150 2.0, Uvinul® A+2.80, $TiO_2$ 2.0 (100 to 200 nm); radical scavenger tocopherylacetate 0.8; other common accompanying substances.

Sun protection cream II: Composition as in example 2.

It is found that the number of free radicals on the skin is distinctly reduced by the sun protection cream II of the invention.

The untreated skin shows under radiation with a sun simulator or with a water-filtered IR lamp, respectively, a high radical formation for skin type I-III. In the UV range the radical formation is three times higher (radical formation=0.12 in relative units) than for skin type V (radical formation=0.4 rel. units). However, in the near-IR wavelength range are formed two times more free radicals (radical formation=0.04 rel. units) in dark skin than in light skin (radical formation=0.02 rel. units).

Tests show that under application of the commercial sun protection cream I in the UV range the radical formation in light skin is reduced below 0.01 rel. units by the UV filters. The same takes place also for dark skin. In the near-IR range the radical formation for both skin types is reduced a little in comparison with the untreated skin. The radical formation in the near-IR range is 0.18 rel. units in light skin (reduction by 10%) and in the dark skin 0.36 rel. units (reduction by 10%).

If sun protection cream II of the invention is applied on the skin also a good protection in the UV range is proved. But also in the IR spectral range a significant reduction of the radical formation will be found. For light skin the value of radical formation is reduced to 0.0028 rel. units (reduction of 86%) and for dark skin to 0.0036 rel. units (reduction of 91%). The skin temperature is measured with a contactless IR thermometer before and after radiation and the value is after application of sun protection cream II below 40° C.

The radiation in the near-IR range has taken place with a water-filtered IR lamp in the spectral range of 600 nm to 1400 nm.

Example 5

Cream formulations LC and LC1 have been tested Compositions:

| Phase | Ingredients | % |
|---|---|---|
| | Vehicle | |
| A | DIMETHICONE | 24.0000 |
| | CYCLOPENTASILOXANE, CYCLOHEXASILOXANE | 2.5000 |
| | DISTEARDIMONIUM HECTORITE | 0.5000 |
| | ISODODECANE | 6.0000 |
| | ETHYLHEXYL METHOXYCINNAMATE | 7.5000 |
| | ISOPROPYL MYRISTATE | 3.0000 |
| | OCTOCRYLENE | 2.0000 |
| | DEXTRIN PALMITATE | 0.3000 |
| | CYCLOPENTASILOXANE | 1.0000 |
| | DIISOPROPYL SEBACATE | 2.0000 |
| | POLYMETHYLSILSESQUIOXANE | 2.0000 |
| | PEG-9 POLYDIMETHYLSILOXYETHYL DIMETHICONE | 1.5000 |
| | DIETHYLAMINO HYDROXYBENZOYL HEXYL BENZOATE | 2.0000 |
| | BIS-ETHYLHEXYLOXYPHENOL METHOXYPHENYL TRIAZINE | 1.0000 |
| | DIISOSTEARYL MALATE | 0.1500 |
| | TOCOPHERYL ACETATE | 0.1000 |
| B | AQUA | qsp 100 |
| | GLYCERIN | 3.0000 |
| | PEG/PPG-17/6 COPOLYMER | 0.5000 |
| | DISODIUM EDTA | 0.0200 |
| | PHENYLBENZIMIDAZOLE SULFONIC ACID | 2.0000 |
| | TRIETHANOLAMINE | qs |
| C | ALCOHOL | 15.0000 |
| | PARFUM | 0.2000 |
| D | PHENOXYETHANOL | 0.1500 |
| | ETHYLHEXYLGLYCERIN | 0.0500 |
| E | ZINC OXIDE | 5.05 |
| | TALC | 2.5 |
| | TITANIUM DIOXIDE | 2.52 |
| LC | Vehicle + cooling agent (0.1% menthol) + antioxidants (*Scutellaria baicalensis* + *Saussurea involucrata*) + *Leucojum aestivum* bulb extract | |
| LC1 | Vehicle + $TiO_2$ 2.52% + green tea extract 0.06% + cooling agent (1% menthol) + antioxidants (*Scutellaria baicalensis* + *Saussurea involucrata*) + *Leucojum aestivum* bulb extract | |

Preparation of the Compositions:

Phases A, B and E are prepared separately, heat at 70° C., and mix carefully by stirring to emulsify the mixture. After cooling down the mixture at 30-35° C., phases C and D are added.

Determination of the Sun Protection Factor (SPF) of LC1:

An SPF of 44 was determined for the formulation LC1 according to the guidelines (ISO 24444).

Example 5-1: Determination of the Radical Protection Factor (RPF) In Vitro

Method:

The principle of the RPF technology is the determination of the radical scavenging activity of a substance/product, which contains antioxidants (T. Herrling, L. Zastrow, and N. Groth, "*Classification of cosmetic products—The Radical Protection Factor (RPF),*" S™ *FW-Journal* 5(124), 282-284 (1998)).

This test is performed by EPR spectroscopy using a test radical, which is reduced by the antioxidative system. The number of reduced test radicals represents the radical scavenging activity that is normalized to 1 mg input of the antioxidant substance/product. The RPF is calculated by the following equation (1):

$$RPF = \frac{RC \cdot RF}{PI} \quad (1)$$

RC=concentration of the test radical [radicals/ml]

RF=The reduction factor represents the difference between the untreated test radical intensity and the decreased signal intensity after treatment with the antioxidant normalized to the signal of the untreated test radical.

PI=Product input represents the amount of the substance/product measured in [mg/ml]

The RPF is expressed by a positive number N with the measuring unit $10^{14}$ radicals/mg, which means:

RPF=N·[$10^{14}$ radicals/mg].

For the RPF analysis a X-Band EPR spectrometer (MS5000, Magnettech GmbH by Freiberg Instruments GmbH, Freiberg, Germany) was used to analyze the reduction of the test radical 2,2-Diphenyl-1-picrylhydrazyl DPPH (Sigma-Aldrich, Steinheim, Germany) by the antioxidative system. The calculation of the spin concentration of the 1 mM ethanolic DPPH solution was performed by a X-Band EPR spectrometer from Bruker BioSpin GmbH (Bruker Elexsys E500, Karlsruhe, Germany) as previously described (8). The analysis of the EPR data was performed using the Bruker device control software Xepr (Bruker Biospin, Karlsruhe, Germany). The spin quantification was performed according to procedure detailed in the Xepr manual (Bruker Biospin, Karlsruhe, Germany). The absolute spin concentrations and the spin amounts were calculated in triplicates.

For the RPF analysis of the samples, 500 mg of the formulations were solubilized in 10 mL ethanol, followed by a dilution (1:1) with a 1 mM DPPH ethanolic solution of known spin concentration. The samples were kept dark at room temperature by constant panning. The measurements took place directly after sample preparation (0 hours) and 23 to 28 hours after sample incubation, until stabilization of the DPPH signal. The calculation of the RPF value was performed by using the EPR software "ESR Studio" (Freiberg Instruments GmbH, Freiberg, Germany) and the calculation program Microsoft Excel 2016 2016 (Microsoft Office 2016).

Results:

| Compositions | RPF in $10^{14}$ radicals/mg |
|---|---|
| LC | 48 |
| LC1 | 33 |

LC and LC show good RPF values.

Example 5-2: Evaluation of the Optical Properties (In Vitro)

Method:

The optical parameters $\mu_a$ and $\mu_s'$ were calculated by inverse Monte Carlo simulation (iMCS) (Reference: M Friebel et al., "*Determination of optical properties of human blood in the spectral range* 250 *to* 1100 *nm using Monte Carlo simulations with hematocrit-dependent effective scattering phase function,*" *Journal of Biomedical Optics* 11(3), (2006)).

The iMCS uses forward Monte Carlo simulations iteratively to calculate the optical parameters $\mu_a$ and $\mu_s'$ on the basis of a given phase function and the experimentally measured values for reflection and transmission ($R_t^M$ and $T_t^M$). The iMCS uses a start set of $\mu_a$ and $\mu_s'$ to calculate the resulting simulated reflectance and transmission values $R_t^S$, and $T_t^S$. These values are then compared to the $R_t^M$ and $T_t^M$ values, measured experimentally. By systematic variation of $\mu_a$ and $\mu_s'$ the deviation of the simulated $R_t^S$ and $T_t^S$ values from the ones measured is minimized until a set of optical parameters is found, where the deviations are within an error threshold of 0.20%. For the refractive index of the formulations, the values for water were used and an isotropic scattering was used to calculate $\mu_s'$.

The investigations were done for the sunscreen formulations LC and LC1.

Results:

Both creams, LC and LC1, were prepared two times and each sample was three times measured. The spectra for each sample were averaged and dependently simulated.

Figure 1:
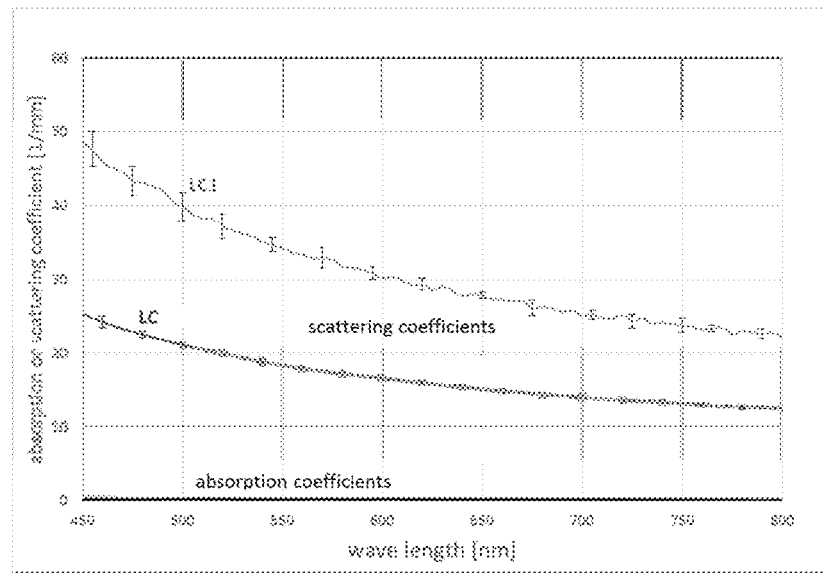
FIG. 1: Optical properties absorption ta and scattering effective coefficient μs' of the formulation LC and LC1

Cream LC shows medium scattering parameters decreasing with increasing wavelength; cream LC1 represents a further development with doubling of the scattering properties (FIG. 1).

Example 5-3: Radical Formation after VIS/NIR Irradiation (Ex Vivo)

Method: EPR Investigations: Prevention of the Radical Formation in the VIS/NIR Spectral Regions Sample Preparation and EPR Measurements The EPR technology enables measurements of free radicals within the skin, induced by exogenous stressors, like irradiation by using the spin marker PCA (3-(carboxy)-2,2,5,5-tetramethylpyrrolidin-1-oxyl). It could be shown by this method that different spectral regions show different strong tendencies in the radical production in vivo as well as ex vivo. UV light promoted the strongest radical formation, followed by VIS and NIR irradiation. UV is responsible for at least 50% of ROS formation, the remaining radicals are produced by the VIS/NIR radiation.

In this study, porcine ear skin, which is a suitable model for human skin, was used to analyze the radical protection effect of two sunscreen formulations (LC and LC1).

X-Band EPR is a suitable and reproducible technique for analyzing skin samples with and without irradiation in a defined manner. This method is established and has already been published (C. Souza et al., "*Radical-Scavenging Activity of a Sunscreen Enriched by Antioxidants Providing Protection in the Whole Solar Spectral Range,*" Skin Pharmacol Physiol 30(2), 81-89 (2017)).

For the testing of the various cream formulations, 2.0 mg/cm$^2$, according to the COLIPA standard procedure, were distributed evenly onto the skin surface by massage (Rehaforum Medical GmbH, Elmshorn, Germany) for 2 min. The EPR investigations were performed 30 minutes after application time. Skin biopsies were treated as previously described followed by EPR investigations.

For the evaluation, the signal amplitude of PCA was determined from each spectrum by the evaluation software "ESR Studio". The amount of PCA could be derived from the signal height of the central line of the spectrum, since the line shape of the EPR spectrum remained unchanged over the measured time period. To calculate the radical formation, the EPR intensity of the irradiated samples was subtracted from samples without irradiation. Also, irradiated and non-irradiated control biopsies without any cream application were analysed.

Each experiment was repeated in duplicate, on 6 porcine ears.

Results:

LC1 reduces the radical formation by 53%, LC by 28% in skin in comparison to the untreated skin (FIG. 2).

Example 5-4: NIR Protection

Method: Determination of the Influence of NIR Irradiation on the Antioxidative Network of Skin To analyze the NIR protection of the sunscreen formulation LC and LC1, the carotenoid concentration was determined in skin by resonance Raman spectroscopy (RRS) in vivo.

Two skin areas of the inner forearm of 6 female volunteers (skin type IV-V, according to the Fitzpatrick scale (T B. Fitzpatrick "*The Validity and Practicality of Sun-Reactive Skin Type-I Through Type-Vi,*" Arch. Dermatol. 124(6), 869-871 (1988))) were analyzed regarding their carotenoid levels. One skin area remain untreated, the other skin area was evenly treated with the cream formulations LC and LC1, respectively (according to the COLIPA standard procedure). The carotenoid levels were determined after 30 min penetration time before irradiation, and 60 min after NIR irradiation. The irradiance was 60 mW/cm$^2$ and was applied for 30 min.

Results:

To analyze the protection of the cream formulations LC and LC1 in the NIR spectral region with regard to the antioxidant status, the carotenoid levels were investigated by resonance Raman spectroscopy non-invasively in vivo (FIG. 3).

Former investigations have demonstrated that carotenoids could serve as a marker substance of the antioxidant status of the human skin.

For untreated skin, the carotenoid level decreases after 60 min NIR irradiation. In contrast to this result, an application of the cream formulations LC and LC1 respectively promote an increase of the carotenoid levels in both cases significantly (p≤0.05, FIG. 3). Thus, the antioxidant status was not only stabilized, the antioxidant status was even improved. These results strongly indicate that both sunscreens, LC and LC1, provide a very good radical protection in the NIR spectral regions; LC1 support the antioxidant network a little bit stronger. NIR irradiation reduces carotenoids in the skin. The included antioxidants within the cream formulations support the antioxidative network of the skin, showing that antioxidants in the skin can be effectively enhanced by the topical application of the new developed sunscreen formulations.

Example 6: Example of a Sun Protection Milk Formulation

| Sun protection milk W/Si | % |
|---|---|
| Dimethicone, Dimethicone PEG 10/15 crosspolymer | 3 |
| Cyclopentasiloxane, Dimethicone/vinyl Dimethicone crosspolymer | 2 |
| Dimethicone | 5 |
| Cyclopentasiloxane | 5 |
| PEG-9 Polydimethylsiloxethyl Dimethicone | 1 |
| Isotridecyl isononanoate | 4 |
| Ethylhexyl methoxy cinnamate | 5 |
| BIS-ETHYLHEXYLOXYPHENOL METHOXYPHENYL TRIAZINE | 2 |
| TiO2 | 10 |
| Isononyl isononanoate | 15 |
| Cyclopentasiloxane/cyclohexasiloxane | 15 |
| Cetyl dimethicone | 6 |
| Sodium chloride | 1 |
| TiO2 | 10 |
| Propylene glycol | 2 |
| Menthol | 0.1 |
| Alcohol | 10 |
| Green tea | 0.04 |
| *Scutellaria Baicalensis* | 0.02 |
| *SAUSSUREA INVOLUCRATA* EXTRACT | 0.01 |
| preservative | qsp |
| aqua | ad 100 |

Example 7: Example of a Sun Protection Gel Formulation

| Sun protection gel | % |
|---|---|
| Octocrylene | 10 |
| Ethylhexyl salicylate | 5 |
| Butyl methoxydibenzoylmethane | 2 |
| Diethylamino Hydroxybenzoyl Hexyl Benzoate | 1 |
| PVP/hexadecene copolymer | 1 |
| Dicapiylylcarbonate | 6 |
| Stearoxy dimethicone | 1.2 |
| Cyclopentasiloxane/cyclohexasiloxane | 3 |
| TiO2 | 5 |
| ZnO | 2 |
| Green tea | 0.06 |
| *Scutellaria Baicalensis* | 0.01 |
| Menthol | 1 |
| Alcohol | 8 |
| Acrylates copolymer | 2 |
| Disodium EDTA | qsp |
| Sodium hydroxide | qsp |
| Aqua | ad to 100 |

Example 8: Example of a Sun Protection Lotion Formulation

| Sun protection lotion | % |
| --- | --- |
| TiO2 | 6 |
| ZnO | 1 |
| Arachidyl alchol, benyl alcohol, arachidyl glucoside | 3.5 |
| Myristyl alcohol, myristyl glucoside | 1.5 |
| C12-C15 Alkyl benzoate | 6 |
| Octocrylene | 8 |
| Ethylhexyl Triazone | 2 |
| Butyl methoxydibenzoylmethane | 1 |
| Isohexadecane | 4 |
| Caprylic/capric triglyceride | 10 |
| Green tea | 0.04 |
| *Scutellaria Baicalensis* | 0.01 |
| *SAUSSUREA INVOLUCRATA* EXTRACT | 0.01 |
| Menthol | 0.5 |
| Alcohol | 10 |
| Propylene glycol | 5 |
| Xanthan gum | 0.3 |
| Aqua | qsp 100 |

Example 9: RPF Evaluations

We carry out the evaluation of ROS (Reactive Oxygen species) formation according to the previously described method of the following samples:

1% of menthol

The following mixture of antioxidants used in the LC1 composition: mixture of *Scutellaria baicalensis* root extract, *Saussurea involucrata* extract, *Leucojum aestivum* bulb extract and green tea extract The association of the above-described mixture of antioxidants and 1% of menthol for the synergistic effect of the composition ingredients.

Example 10: RPF Evaluations

We carry out the evaluation of ROS formation according to the previously described method of the following samples:

the composition LC1
the composition LC1 without 1% menthol
for the synergistic effect of the composition ingredients.

The invention claimed is:

1. A composition having antioxidant and visible and near infra-red light protection properties comprising a mixture of the following substances, the respective percentages by weight being in relation to the total weight of the composition
   a) one or more UVA and UVB filters at a percentage by weight from 5 to 24%,
   b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
   c) one or more cooling agents at a percentage by weight from 0.1 to 20%
   d) one or more radical scavengers at a percentage by weight from 0.1 to 48%, or from 0.1 to 5%, and
   e) a residual percentage up to 100 wt % of cosmetic carriers, excipients, active substances and mixtures thereof, wherein the radical scavenger is a mixture of *Rhodiola Sacra* Root Extract, *Coix Lacryma-Jobi* Seed Extract, *Dendrobium nobile* Lindl Flower Extract and *Camellia sinensis* Leaf Extract, or wherein the radical scavenger is a mixture of *Saussurea involucrata* Extract, *Calendula officinalis* Flower Extract, *Paeonia lactiflora* Root Extract and *Camellia sinensis* Leaf Extract, or wherein the radical scavenger is a mixture of *Scutellaria lateriflora* Root Extract, *Salvia miltiorrhiza* Root Extract, *Bletilla striata* Root Extract and *Camellia sinensis* Leaf Extract.

2. The composition according to claim 1, which is a cosmetic light protection and sunscreen composition.

3. The composition according to claim 1, which is an anti-aging composition.

4. The composition according to claim 1, which is an anti-dark spot composition.

5. The composition according to claim 1, which is a whitening composition, said composition comprising a whitening agent.

6. The composition according to claim 1, comprising a mixture of the following substances, the respective percentages by weight being in relation to the total weight of the composition
   a) one or more UVA and UVB filters at a percentage by weight of 14.5%,
   b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight from 2 to 30%,
   c) one or more cooling agents at a percentage by weight from 0.1 to 20%,
   d) one or more radical scavengers at a percentage by weight from 0.1 to 5%, and
   e) a residual percentage up to 100 wt % of cosmetic carriers, excipients, active substances and mixtures thereof, or comprising a mixture of the following substances, the respective percentages by weight being in relation to the total weight of the composition
   a) one or more UVA and UVB filters at a percentage by weight from 5 to 24%,
   b) one or more pigments, selected from the group consisting of rutile (titanium dioxide), zinc oxide, silicon dioxide, zirconium oxide, aluminium oxide and mixtures thereof having different particle sizes in the micro and nano ranges and at a percentage by weight of 10.5%,
   c) one or more cooling agents at a percentage by weight from 0.1 to 20%,
   d) one or more radical scavengers at a percentage by weight from 0.1 to 5%, and
   e) a residual percentage up to 100 wt % of cosmetic carriers, excipients, active substances and mixtures thereof.

7. The composition according to claim 1, wherein the UV filters are Bis-Ethylhexyloxyphenol Methoxyphenyl Triazine, Drometrizole Trisiloxane, Terephthalylidene Dicamphor Sulfonic Acid, Ethylhexyl Triazone, Butyl Methoxydibenzoylmethane, Diethylamino Hydroxybenzoyl Hexyl Benzoate, Diethylhexyl Butamido Triazone, Phenylbenzimidazole Sulfonic Acid, Ethylhexyl Methoxycinnamate, Ethylhexyl Salicylate, Methylene Bis-Benzotriazolyl Tetramethylbutylphenol, Octocrylene, Phenylbenzimidazole Sulfonic Acid, or mixtures thereof, or wherein the UV filters are a mixture of Ethylhexyl Methoxycinnamate, Diethylamino Hydroxybenzoyl Hexyl Benzoate, Bis-Ethylhexyloxyphenol Methoxyphenyl Triazine, Octocrylene and Phenylbenzimidazole Sulfonic Acid.

8. The composition according to claim 1, wherein the pigment is a mixture of nanometer-size particles and micrometer-size particles in a weight ratio of the nanoparticles to the microparticles from 5:1 to 8:1.

9. The composition according to claim 1, wherein the cooling agent is selected from the group consisting of L-Menthone Glycerol Ketal, DL-Menthone Glycerol Ketal, mixtures of the two, N-Ethyl-p-Menthane-3-Carboxamide, Menthol, Isopulegol, Monomenthyl Glutarate, 3-L-Menthoxypropane-1,2-Diol, Ethoxycarbonylmethyl-3-p-Menthane Carboxamide, essential oils of camphor, mint, lavender and mixtures thereof.

10. The composition according to claim 1, wherein the radical scavenger has a radical protection factor of 40 to 100,000.

11. The composition according to claim 1, having a radical protection factor of 20 to 4,000.

12. The composition according to claim 1, having a sun protection factor higher than 40, or of 40 to 50+.

13. The composition according to claim 1, being in a form of milk, gel, lotion, stick, water in oil emulsion, oil in water emulsion, or fluid emulsion.

* * * * *